US00PP23796P3

(12) United States Plant Patent
Zaiger et al.

(10) Patent No.: US PP23,796 P3
(45) Date of Patent: Aug. 6, 2013

(54) INTERSPECIFIC TREE NAMED 'SWEET PIXZEE 2'

(50) Latin Name: ***Interspecific Prunus* species**
Varietal Denomination: Sweet Pixzee 2

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 85 days.

(21) Appl. No.: 13/374,093

(22) Filed: Dec. 12, 2011

(65) Prior Publication Data

US 2013/0152251 P1 Jun. 13, 2013

(51) Int. Cl.
*A01H 5/00* (2006.01)

(52) U.S. Cl.
USPC ..... Plt./180

(58) Field of Classification Search
USPC ..... Plt./180
See application file for complete search history.

*Primary Examiner* — Annette Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1) Vigorous, upright tree growth.
2) Heavy and regular bearer of medium size fruit.
3) Fruit with very good flavor and eating quality.
4) Fruit with good handling and shipping quality.
5) Fruit with an average Brix of 17.8° with a good balance between acid and sugar.

1 Drawing Sheet

Botanical classification: Interspecific *Prunus* species.
Variety denomination: 'Sweet Pixzee 2'.

BACKGROUND OF THE VARIETY

1. Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

2. Prior Varieties

Among the existing varieties of cherry and interspecific species, which are known to us, and mentioned herein, 'Tri-Lite' Interspecific (U.S. Plant Pat. No. 8,393), the proprietary cherry selection '101EB486' (non-patented) and the proprietary non-patented interspecific selections '178LM74', '125LE383' and '5ZA500'.

STATEMENT REGARDING FEDERALLY SPONSORED RESEARCH AND DEVELOPMENT

Not applicable.

ORIGIN OF THE VARIETY

The new and distinct variety of interspecific tree [(*Prunus salicina*×(*Prunus salicina*×*Prunus armeniaca*))×*Prunus avium*]×[*Prunus salicina*×(*Prunus salicina*×*Prunus persica*)] was originated by us in our experimental orchard located near Modesto, Calif. as a first generation cross between our proprietary interspecific selections; '178LM74' (non-patented) and '5ZA500' (non-patented). The seed parent '178LM74' (non-patented) originated as a first generation cross between our proprietary interspecific seedling selection '125LE583' (non-patented) and our proprietary cherry seedling selection '101EB486' (non-patented). The pollen parent '5ZA500' (non-patented) originated from crosses between the following; 'Tri-Lite' Interspecific (U.S. Plant Pat. No. 8,393) and the proprietary interspecific seedling selection '150LB26' (non-patented). A large number of these first generation seedlings growing on their own root system, were budded to older trees of 'Nemaguard' Rootstock (non-patented) to induce earlier maturity and fruit evaluation. Under close and careful observation one such seedling exhibited desirable fruit and tree characteristics and was selected in 2005 for additional asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree [(Plum×Plumcot)×Cherry]×[Plum×(Plum×Peach)] is of large size, vigorous, upright growth and a productive and regular bearer of medium size, yellow flesh, firm fruit with very good flavor and eating quality. The fruit is further characterized by holding firm on the tree three weeks past maturity (shipping ripe) and having good storage and shipping quality. In comparison to its seed parent '178LM74' (non-patented) the fruit of the new variety has red skin color compared to yellow and is larger in size. In comparison to the pollen parent '5ZA500' (non-patented) the fruit of the new variety is smaller in size and is approximately 18 days earlier in maturity. In comparison to the commercial interspecific variety 'Dapple Supreme' (U.S. Plant Pat. No. 16,412) the fruit of the new variety has yellow flesh compared to red, is smaller in size and is approximately 5 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size*.—Large, pruned to 3 to 3.5 meters in height and width for economical harvesting of fruit. Varies with different cultural practices.

*Vigor*.—Vigorous, tree growth of approximately 1.5 to 2 meters the first growing season. Varies with cultural practices, soil type, fertility and climatic conditions.

*Form*.—Upright growth, usually pruned to vase shape.

*Branching habit*.—Upright, crotch angle approximately 30°, increases with heavy crop load.

*Productivity*.—Productive, thinning and spacing of fruit desirable for market size fruit. Fruit set varies with climatic conditions during bloom season.

*Bearer*.—Regular, adequate fruit set 4 consecutive years. No alternate bearing observed.

*Fertility*.—Self-sterile, pollinator required.

*Density*.—Medium dense, usually pruned to vase shape to increase sunlight and air movement to center of tree to enhance fruit color and health of fruit spurs.

*Hardiness*.—Hardy in all stone fruit growing areas of California. Tree grown in USDA Hardiness Zone 9. Winter chilling requirement approximately 850 hours at or below 45° F.

Trunk:

*Size*.—Medium to large. Average circumference 50.8 cm at 25.4 cm above ground level on a 6 year old tree.

*Stocky*.—Medium stocky.

*Texture*.—Medium shaggy, becomes rougher with age.

*Color*.—Varies from 7.5YR 4/8 to 10YR 5/8.

Branches:

*Size*.—Medium. Average circumference 14.7 cm at 1.0 meter above ground. Crotch angle approximately 30°, increases with heavy crop load.

*Surface texture*.—New growth relatively smooth. Mature growth medium rough, roughness increases with age.

*Lenticels*.—Size — medium. Average number 52 in a 25.8 sq cm area. Average length 2.9 mm. Average width 0.8 mm. Color varies from 5YR 6/10 to 7.5YR 6/8.

*Color*.—New growth 5GY 5/8. Old growth varies from 7.5YR 2/4 to 10YR 4/2, varies with age of growth.

Leaves:

*Size*.—Medium. Average length 84.6 mm. Average width 36.5 mm.

*Form*.—Elliptical.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 13.1 mm. Average width 1.1 mm. Longitudinally grooved. Very short pubescence. Color — 5GY 4/6.

*Glands*.—Globose. Size — very small. Average length 0.5 mm. Average diameter 0.2 mm. Average number — 2, varies from 1 to 3. Located primarily on the upper portion of the petiole and base of leaf blade. Color varies from 2.5GY 6/6 to 5GY 6/6.

*Stipules*.—Average number 2. Average length 4.9 mm. Margin — serrate. Color varies from 5GY 7/6 to 5GY 6/6.

*Color*.—Upper surface varies from 5GY 3/6 to 7.5GY 3/4. Lower surface varies from 5GY 5/4 to 7.5GY 4/4. Midvein color varies from 2.5GY 6/6 to 5GY 7/6.

Flower buds:

*Size*.—Medium. Average length 10.4 mm. Average diameter 5.1 mm.

*Hardiness*.—Hardy with respect to California winters.

*Form*.—Conical, becoming slightly elongated before opening.

*Pedicel*.—Average length 9.9 mm. Average width 0.6 mm. Color varies from 2.5GY 6/8 to 5GY 6/8. Surface — glabrous.

*Color*.—N 9.5/ (white).

Number of buds per spur: Average number 9, varies from 8 to 13. Varies with age of spur.

Flowers:

*Blooming period*.—Date of First Bloom Feb. 28, 2010. Date of Petal Fall Mar. 7, 2010, varies slightly with climatic conditions.

*Size*.—Medium. Average height 11.4 mm. Average diameter 16.4 mm.

*Petals*.—Size — medium. Number — normally 5, alternately arranged to sepals. Average length 9.7 mm. Average width 7.4 mm. Form — varies from globose to slightly elongated. Margin — sinuate. Color — N 9.5/ (white). Both upper and lower surfaces glabrous.

*Sepals*.—Number — normally 5, alternately arranged to petals. Size — medium. Average length 3.4 mm. Average width 2.3 mm. Form — triangular, apex rounded. Margin — entire. Color — upper surface varies from 5GY 6/6 to 5GY 6/8. Lower surface varies from 5GY 6/6 to 7.5GY 6/6. Both upper and lower surface glabrous.

*Stamens*.—Average number per flower 29. Average filament length 8.8 mm. Filament color N 9.5/ (white). Anther color varies from 5Y 8/10 to 5Y 7/12.

*Pollen*.—Self sterile, pollinator required. Color varies from 2.5Y 7/10 to 2.5Y 7/12.

*Pistil*.—Normally one. Surface — glabrous. Average length 11.2 mm. Stigma height approximately 0.9 mm above anthers. Color varies from 10Y 8.5/6 to 2.5GY 8/8.

*Fragrance*.—Heavy aroma.

*Color*.—N 9.5/ (white).

*Number of flowers per flower bud*.—Average number 2, varies from 1 to 3.

*Pedicel*.—Average length 10.9 mm. Average width 0.7 mm. Color varies from 2.5GY 6/8 to 5GY 7/8. Surface — glabrous.

Fruit:

*Maturity when described*.—Firm ripe.

*Date of first picking*.—Jun. 24, 2010.

*Date of last picking*.—Jul. 2, 2010, varies slightly with climatic conditions.

*Size*.—Medium. Average diameter axially 49.2 mm. Average transversely in suture plane 46.8 mm. Average weight 59.6 grams, varies slightly with fertility of the soil, amount of thinning and climatic conditions.

*Form*.—Slightly elongated to globose.

*Suture*.—Nearly smooth.

*Ventral surface*.—Nearly smooth.

*Apex*.—Nearly rounded.

*Base*.—Flat.

*Stem cavity*.—Rounded to slightly elongated in suture plane. Average depth 1.5 mm. Average diameter 2.7 mm.

Stem:

*Size*.—Large. Average length 19.8 mm. Average diameter 2.1 mm.

*Color*.—2.5GY 6/8.

Flesh:

*Ripens*.—Evenly.

*Texture*.—Firm, meaty.

*Fibers*.—Few, small, tender.

*Firmness*.—Good, comparable to commercial plum varieties.

*Aroma*.—Slight.

*Amydgalin*.—Undetected.

*Eating quality*.—Very good.

*Flavor*.—Very good, good balance between acid and sugar.

*Juice*.—Heavy amount, enhances flavor.

*Brix*.—Average 17.8°, varies slightly with amount of fruit per tree and climatic conditions.

*Color*.—Varies from 5Y 8/6 to 5R 4/14 next to skin.

*Pit cavity*.—Ovoid to globose. Average length 24.2 mm. Average width 15.8 mm. Color varies from 5Y 7/6 to 5YR 6/6.

Skin:

*Thickness*.—Medium.

*Surface*.—Smooth.

*Bloom*.—Moderate amount.

*Tendency to crack*.—None.

*Color*.—Ground color varies from 5Y 8/6 to 7.5Y 7/6. Overspread with 7.5R 3/10 to 7.5R 3/12. Very small, randomly spaced areas of exposed ground color giving a speckling pattern to surface.

*Tenacity*.—Tenacious to flesh.

*Astringency*.—Undetected.

Stone:

*Type*.—Clingstone.

*Size*.—Medium. Average length 22.0 mm. Average width 14.2 mm. Average thickness 8.5 mm.

*Form*.—Obovoid.

*Base*.—Flat.

*Apex*.—Pointed. Average length 1.3 mm.

*Surface*.—Very small pits throughout.

*Sides*.—Unequal, one side extending further from suture plane.

*Ridges*.—A small narrow ridge on each side of suture extending from base to apex.

*Tendency to split*.—None.

*Color*.—Varies from 7.5YR 5/6 to 10YR 5/8 when dry.

Kernel:

*Size*.—Medium. Average length 15.3 mm. Average width 8.9 mm. Average depth 5.1 mm.

*Form*.—Ovoid.

*Viability*.—Viable, complete embryo development.

*Skin*.—Color varies from 5Y 9/4 to 7.5Y 9/4.

Use: Dessert.

*Market*.—Local and long distance.

Keeping quality: Good, held firm in cold storage for 3 weeks at 38° to 42° F. without shriveling, internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

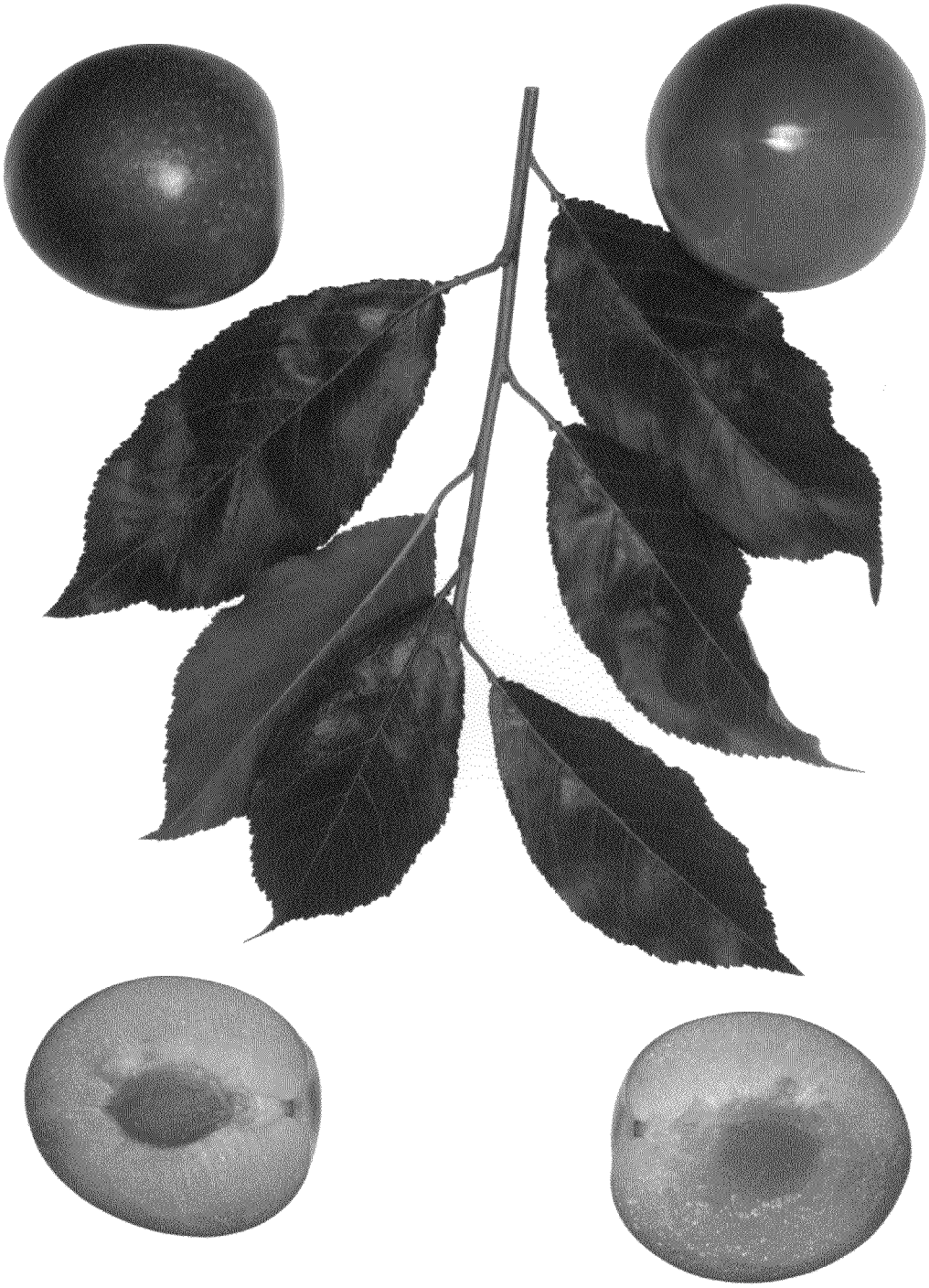

* * * * *